United States Patent
Jones et al.

(10) Patent No.: US 9,308,010 B2
(45) Date of Patent: Apr. 12, 2016

(54) SURGICAL ROTARY CAPTURE INSTRUMENT FOR GASTRIC BAND CLOSING

(75) Inventors: Daniel B. Jones, Wayland, MA (US); Jerry R. Griffiths, Pembroke, MA (US); Francis J. DiFrancesco, Foxboro, MA (US)

(73) Assignee: Specialty Surgical Instrumentation Inc., Antioch, TN (US)

( * ) Notice: Subject to any disclaimer, the term of this patent is extended or adjusted under 35 U.S.C. 154(b) by 1952 days.

(21) Appl. No.: 12/370,956

(22) Filed: Feb. 13, 2009

(65) Prior Publication Data
US 2009/0157104 A1   Jun. 18, 2009

Related U.S. Application Data

(63) Continuation of application No. 11/316,194, filed on Dec. 22, 2005, now abandoned.

(51) Int. Cl.
| | | |
|---|---|---|
| *A61B 17/10* | (2006.01) | |
| *A61B 17/28* | (2006.01) | |
| *A61F 5/00* | (2006.01) | |
| A61B 17/12 | (2006.01) | |
| A61B 17/068 | (2006.01) | |
| A61B 17/115 | (2006.01) | |

(52) U.S. Cl.
CPC .............. *A61B 17/282* (2013.01); *A61F 5/0003* (2013.01); *A61F 5/005* (2013.01); *A61F 5/0089* (2013.01); *A61B 17/068* (2013.01); *A61B 17/115* (2013.01); *A61B 17/12* (2013.01); *A61B 17/12009* (2013.01); *A61B 17/12013* (2013.01); *A61B 2017/12018* (2013.01)

(58) Field of Classification Search
CPC .. A61B 17/282; A61B 17/068; A61B 17/115; A61B 17/12009; A61B 17/12013; A61B 2017/12018; A61B 17/12; A61F 5/0089; A61F 5/005; A61F 5/0003
USPC ............. 606/1, 139, 140, 148, 157, 158, 159, 606/205–210
See application file for complete search history.

(56) References Cited

U.S. PATENT DOCUMENTS

| | | | | |
|---|---|---|---|---|
| 5,219,357 | A * | 6/1993 | Honkanen et al. ............ | 606/205 |
| 5,282,817 | A * | 2/1994 | Hoogeboom et al. ........ | 606/167 |
| 5,344,428 | A * | 9/1994 | Griffiths ........................ | 606/205 |
| 5,364,410 | A * | 11/1994 | Failla et al. ................... | 606/148 |
| 5,470,328 | A * | 11/1995 | Furnish et al. .................... | 606/1 |
| 5,498,256 | A * | 3/1996 | Furnish .............................. | 606/1 |
| 5,601,604 | A * | 2/1997 | Vincent ........................ | 606/216 |
| 5,620,415 | A * | 4/1997 | Lucey et al. .................... | 604/22 |

(Continued)

*Primary Examiner* — Jing Ou
(74) *Attorney, Agent, or Firm* — Hayes Soloway, P.C.

(57) ABSTRACT

An endoscopic surgical rotary capture instrument is used in minimally invasive laparoscopic surgery for closing a gastric band having a buckle end a free end. The rotary capture instrument includes a pusher end that has a stationary jaw and a movable jaw. The movable jaw is actuated by rotary motion of an inner shaft. The jaws are used to gasp securely and push the tube end of the gastric band after it has been threaded through the buckle end of the band. A hook instrument is used to hold the buckle end securely while the rotary capture instrument is used to push the free end of the gastric band.

8 Claims, 27 Drawing Sheets

(56) References Cited

U.S. PATENT DOCUMENTS

| | | | |
|---|---|---|---|
| 5,601,604 A * | 2/1997 | Vincent | 606/216 |
| 5,620,415 A * | 4/1997 | Lucey et al. | 604/22 |
| 5,658,298 A * | 8/1997 | Vincent et al. | 606/139 |
| 5,683,359 A * | 11/1997 | Farkas et al. | 604/22 |
| 5,910,148 A * | 6/1999 | Reimels et al. | 606/144 |
| 6,045,561 A * | 4/2000 | Marshall et al. | 606/148 |
| 2002/0138084 A1* | 9/2002 | Weber | 606/139 |
| 2003/0220659 A1* | 11/2003 | Schmieding et al. | 606/148 |
| 2004/0254605 A1* | 12/2004 | DiFrancesco et al. | 606/205 |
| 2009/0157104 A1* | 6/2009 | Jones et al. | 606/142 |

* cited by examiner

SURGICAL ROTARY CAPTURE INSTRUMENT FOR GASTRIC BAND CLOSING

CROSS REFERENCE TO RELATED CO-PENDING APPLICATIONS

This application is a continuation of and claims the benefit of U.S. non-provisional application Ser. No. 11/316,194 filed on Dec. 22, 2005, now abandoned, and entitled SURGICAL ROTARY CAPTURE INSTRUMENT FOR GASTRIC BAND CLOSING which is commonly assigned and the contents of which are expressly incorporated herein by reference.

FIELD OF THE INVENTION

The present invention relates to an endoscopic surgical rotary capture instrument, and more particularly to a surgical rotary capture instrument used in minimally invasive laparoscopic surgery for closing a gastric band.

BACKGROUND OF THE INVENTION

One method of controlling the intake of food in an obese person is to place an adjustable restriction band 10 around the upper stomach 20, shown in FIG. 1. This creates a new small stomach pouch in the upper stomach 20 for holding a small amount of food and leaves the larger part of the stomach below the band so the stomach volume available for holding food is reduced. The band also controls the stoma, i.e., stomach outlet, between the upper stomach and the lower stomach 30. The size of the stoma regulates the flow of food from the upper stomach to the lower stomach. When the stoma is small the patient feels full sooner and has a feeling of satiety that lasts longer.

One specific type of an adjustable restriction band 10 is the LAP-BAND system manufactured by INAMED Corporation, shown in FIG. 2A and FIG. 2B. The LAP-BAND system is described in U.S. Pat. No. 5,601,604, the contents of which are incorporated herein by reference. Referring to FIG. 2A, the gastric band 10 of the LAP-BAND system includes a body portion 11 a head portion 12 and a tail portion 13. The head portion 12 has a buckle 19 with a pull tab 18 and the pull tab 18 has a hole 18a for receiving a post. The tail portion 13 has a tube 14 extending from one end, a triangular shaped member 13a and a conical shaped barb 13b. Tube 14 is in communication with an inflatable member 16 of the inner surface 15 of the body portion 11. The inflatable member 16 is gradually inflated by injecting a saline solution through the tube 14. The inflated member 16 presses against and constricts the stomach wall underlying the band 10. This results in decreasing the diameter of the stoma. The amount of the injected solution controls the size of the inflated member 16 and accordingly the diameter of the stoma.

During a minimally invasive laparoscopic surgical procedure, the tube 14 of the gastric band 10 is pushed through a laparoscopic cannula and is inserted in the patient's abdomen. The gastric band 10 is then placed around the patient's upper stomach and the tail portion 13 is inserted into the buckle 19 thereby forming a ring structure around the upper stomach. The triangular shaped member 13a of the tail portion 13 interlocks with the buckle 19 and prevents the tube 14 from slipping backwards. The process of inserting the tail portion 13 into the buckle 19 requires simultaneously grasping the buckle 19, inserting the tube 14 through the buckle conduit 19a and then pushing the tube 14. Minimally invasive tools are used for performing these mechanical manipulations needed for tightening the gastric band around the upper stomach.

A prior art combination tool for grasping the pull tab 18 and pushing the tube 14 is described in U.S. Pat. No. 5,658,298. This prior art tool includes two elongated slidably mounted cylindrical members and a handpiece. At the distal end of the first cylindrical member there is a post extending downwards that is dimensioned to engage the hole 18a of the tab 18 from the top side, shown in FIG. 6 of U.S. Pat. No. 5,658,298. The second cylindrical member which is slidably mounted with respect to the first cylindrical member has mounted on its distal end a seat or a fork, shown in FIG. 3A of U.S. Pat. No. 5,658,298. This fork is dimensioned to capture protuberances such as the conical barb 13b at the tube end of the band 10 and push the tube 14 through the buckle conduit 19a, while the first cylindrical member engages and pulls on the pull tab 18. Surgeons performing this type of laparoscopic surgery have encountered the problems of the post unintentionally slipping out of the hole 18a and the fork unintentionally releasing the tube end of the band 10 during the band tightening procedure. This requires regrasping the tube end of the band 10 and the tab 18 several times during the procedure which increases both the operation time and the complexity of the operation.

Accordingly there is a need for an improved grasping and pushing tool used in tightening a band having a buckle end and a free end that does not disengage unintentionally and provides better stability and control during the tightening procedure.

SUMMARY OF THE INVENTION

In general, in one aspect, the invention features an endoscopic surgical capture tool used in minimally invasive surgery through a cannula for grasping and tightening a ligature band. The ligature band comprises an elongated strap having a buckle end and a distal end, the buckle end having an aperture and a pull tab having a hole thereon. The elongated strap is configured to encircle an internal organ and the distal end is configured to pass through and lockingly engage the aperture thereby tightening the ligature band around the internal organ. The capture tool comprises an elongated shaft having an outer shaft, a rotatable inner shaft, a capture end and a handle. The capture end is configured to engage a protuberance of the distal end and push the distal end after it has been threaded through the aperture. The capture end comprises a stationary jaw and a rotationally movable jaw and the rotationally movable jaw is actuated by rotational motion of the inner shaft.

Implementations of this aspect of the invention may include one or more of the following features. The elongated shaft is dimensioned to enter one end, pass through and extend beyond the other end of the cannula. The handle comprises a mechanism for actuating the rotational motion of the inner shaft, thereby actuating the rotationally movable jaw. The mechanism comprises squeezing a handle component. The handle comprises a cylindrical body having first and second side indentations opposite to each other and a thumb indentation on a top surface of the cylindrical body, the thumb indentation being aligned with the rotationally movable jaw. The handle further comprises a latch for keeping the rotationally movable jaw closed. The stationary jaw and the rotationally movable jaw form a circle when closed. The stationary jaw and the rotationally movable jaw comprise rounded edges. The stationary jaw and the rotationally movable jaw comprise a metal, ceramic, polymer, Teflon, alloys, rubber or composites. The stationary jaw and the rotationally movable jaw may have inner surfaces that are spherical, sloped, conical, or have one or more steps or grooves. The internal organ may be stomach, artery, intestines, heart, lung, pancreas, kidney, liver or bone.

In general, in another aspect, the invention features an endoscopic surgical capture tool used in minimally invasive surgery through a cannula for grasping an organ or another tool having a circular cross-section. The capture tool comprises an elongated shaft having an outer shaft, a rotatable inner shaft, a capture end and a handle. The capture end is configured to engage a protuberance of the organs or the other tool. The capture end comprises a stationary jaw and a rotationally movable jaw and the rotationally movable jaw is actuated by rotational motion of the inner shaft.

In general, in another aspect, the invention features an endoscopic surgical instrument used in minimally invasive surgery through a cannula for grasping and tightening a ligature band around an internal organ. The ligature band comprises an elongated strap having a buckle end and a distal end, the buckle end having an aperture and a pull tab having a hole thereon. The elongated strap is configured to encircle the internal organ and the distal end is configured to pass through and lockingly engage the aperture thereby tightening the ligature band around the internal organ. The instrument comprises a hook tool configured to engage the hole and pull the pull tab in a first direction while the distal end is threaded through the aperture and pushed opposite to the first direction and a capture tool configured to engage a protuberance of the distal end and push the distal end. The hook tool comprises a hook having a flat portion and a bend portion extending from the flat portion and the flat portion is configured to slide along a flat surface of the pull tab and the bend portion has an inner surface radius matching a radius of the hole. The capture tool comprises a stationary jaw and a rotationally movable jaw and the rotationally movable jaw is actuated by rotational motion of an elongated shaft. The hook tool and the capture tool apply opposing forces on the ligature band for tightening the ligature band around the internal organ.

In general, in another aspect, the invention features a method for tightening a ligature band around an internal organ via minimally invasive surgery. The method comprises first providing a ligature band comprising an elongated strap having a buckle end and a distal end. The buckle end has an aperture and a pull tab having a hole thereon. Next, inserting the ligature band into a patient's body through a minimally invasive cannula and encircling the internal organ with the elongated strap. Next, inserting a surgical hook tool through the cannula. The hook tool comprises an elongated shaft having a hook end and a handle. The hook end comprises a flat portion and a bend portion extending from the flat portion and the flat portion is configured to slide along a flat surface of the pull tab and the bend portion has an inner surface radius matching a radius of the hole. Next, engaging the hole with the hook end. Next, inserting a surgical capture tool through the cannula. The capture tool comprises an elongated shaft having an outer shaft, a rotatable inner shaft, a capture end and a handle. The capture end comprises a stationary jaw and a rotationally movable jaw and the rotationally movable jaw is actuated by rotational motion of the inner shaft. Next, engaging a protuberance in the distal end with the capture tool and inserting the distal end through the aperture. Finally, pulling the pull tab in a first direction with the hook tool while pushing the distal end with the capture tool opposite to the first direction.

Among the advantages of this invention may be one or more of the following. The rotationally movable jaw provides flexibility in capturing an elongated organ, vessel, or other tool having a variety of circular cross-sectional dimensions. The rounded edges of the jaws prevent the jaws from digging and cutting into the organ or tool. The angle between the axis of the elongated shaft and the jaw axis may be varied depending upon the geometry of the organ that needs to be grasped. The inner surfaces of the jaws may be sloped, conical or have one or more steps. These configurations are useful in grasping organs with various cross-sectional geometries. The bend portion of the hook end together with the extension and the flat portion form a C-shaped hook that grasps securely the pull tab. The risk of unintentional disengagement is very low. The extension helps prevent slippage of the hook out of the hole. The inner surface of the bend portion is formed with a radius that matches the inside of the hole in the pull tab. This distributes the pulling force uniformly around the hole and prevents damaging of the pull tab during pulling. The flat portion of the hook end allows the hook end to slide easily underneath or above the pull tab. The capture tool may also be used in non-endoscopic procedures.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 1:
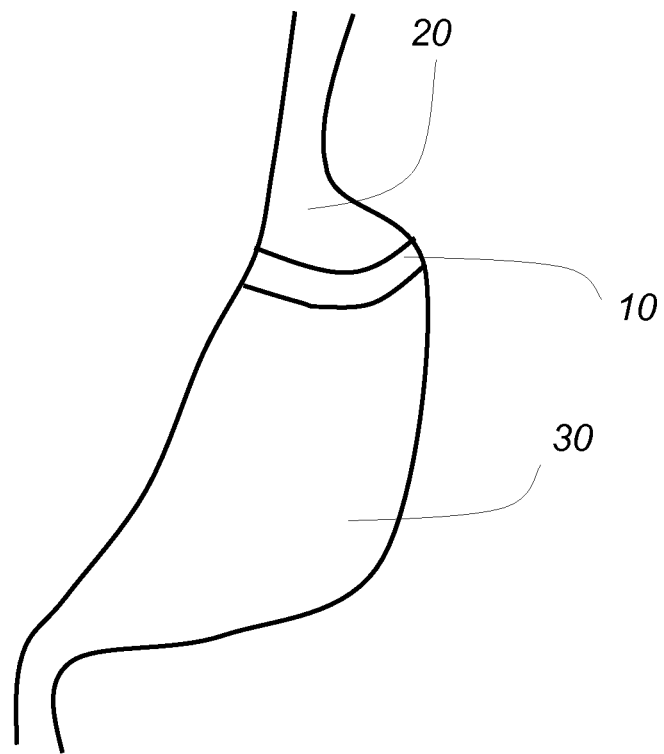
FIG. 1 is a side view of a stomach with an adjustable gastric band around the upper part of the stomach.
Figure 2A:
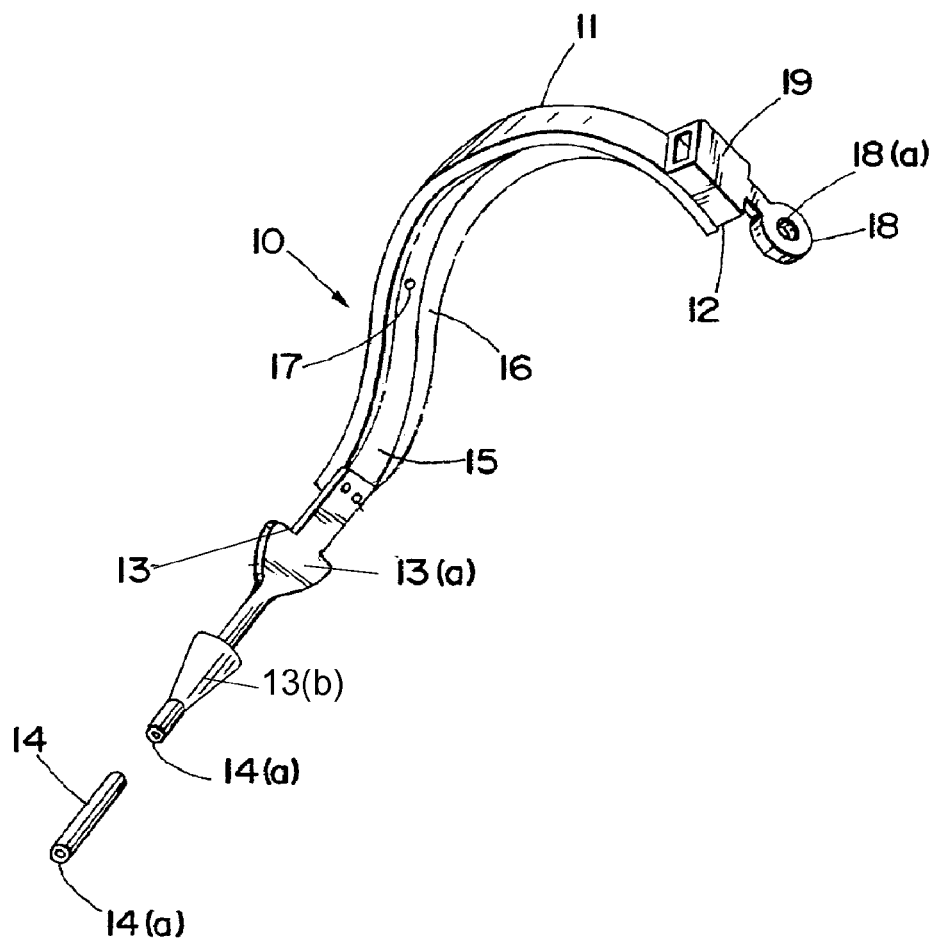
FIG. 2A is a perspective view of an open LAP-BAND gastric band.
Figure 2B:
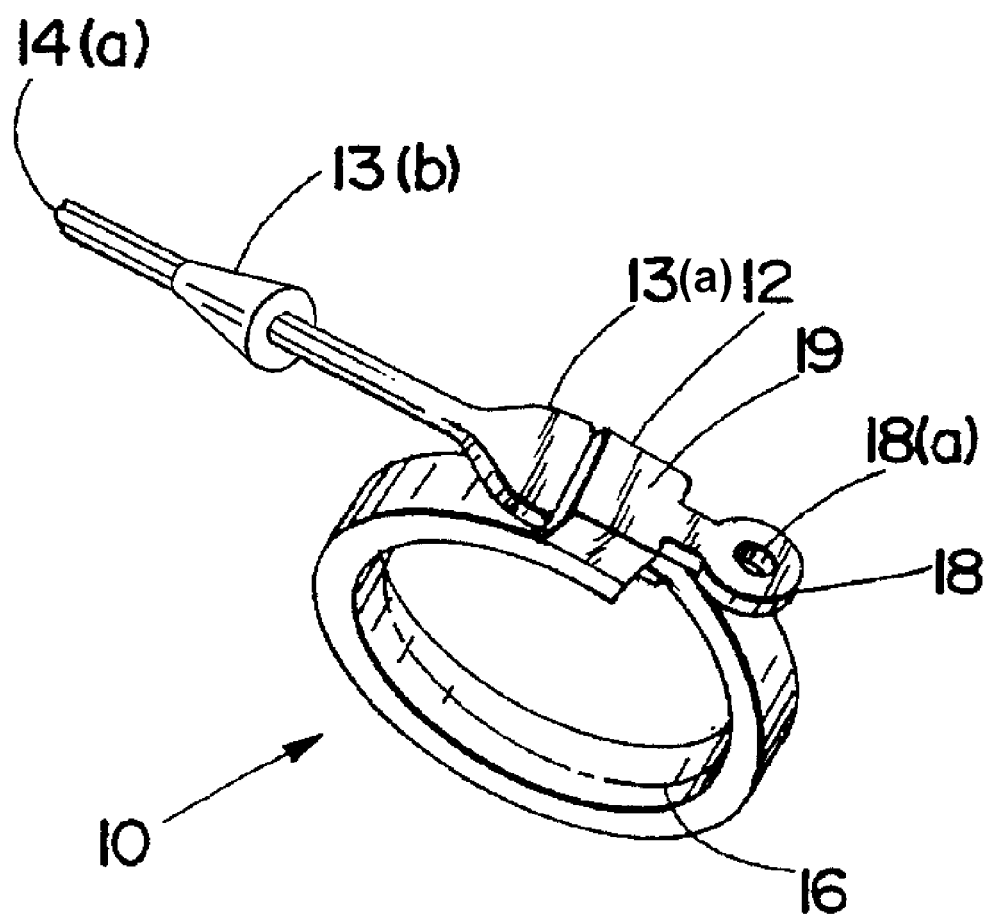
FIG. 2B is the gastric band of FIG. 2A in a closed position forming a ring structure.
Figure 3:
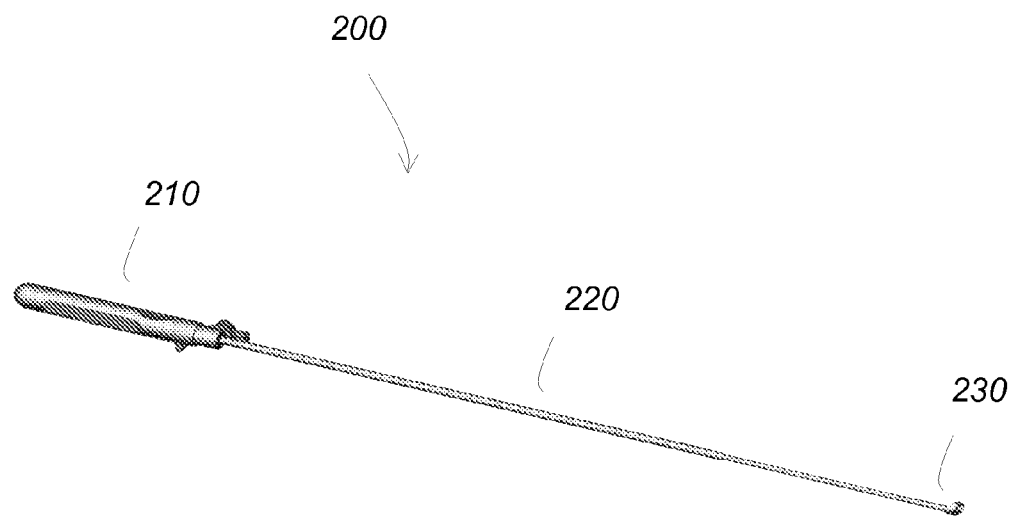
FIG. 3 is a perspective view of the endoscopic rotary capture instrument of this invention.
Figure 4:
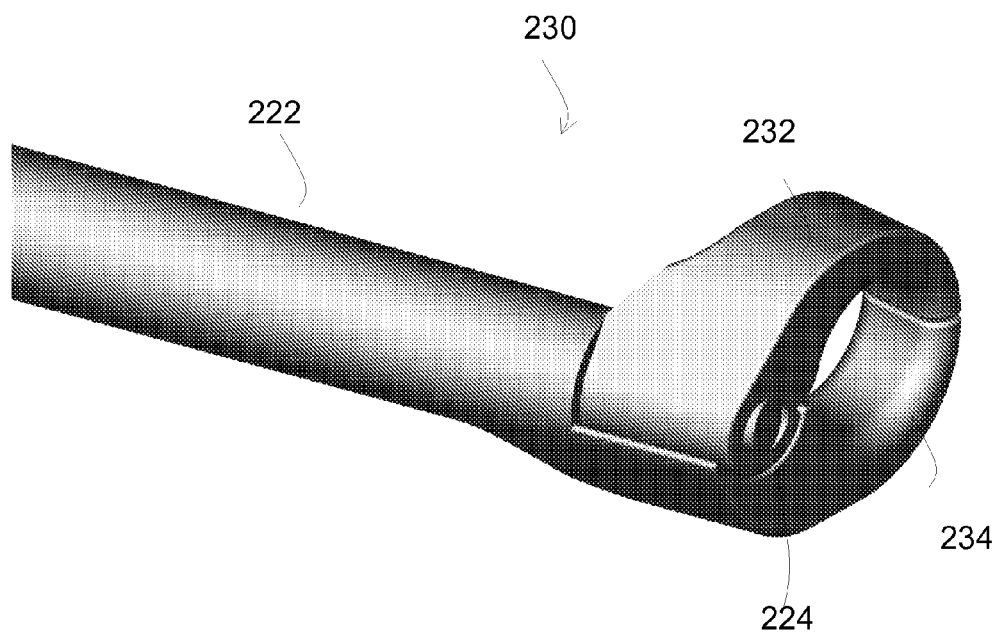
FIG. 4-FIG. 8 are perspective views of the pusher end of the instrument of FIG. 3.
Figure 5:
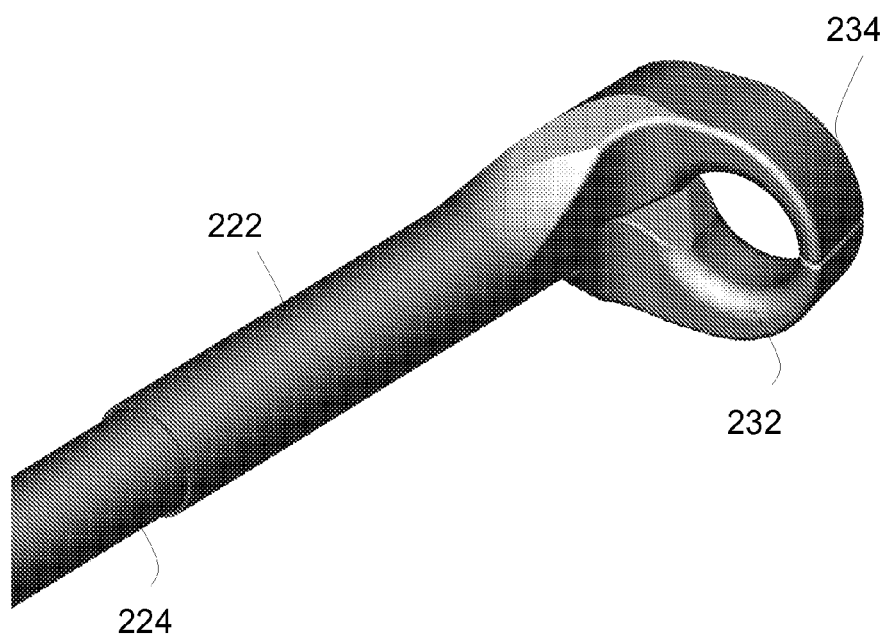
Figure 6:
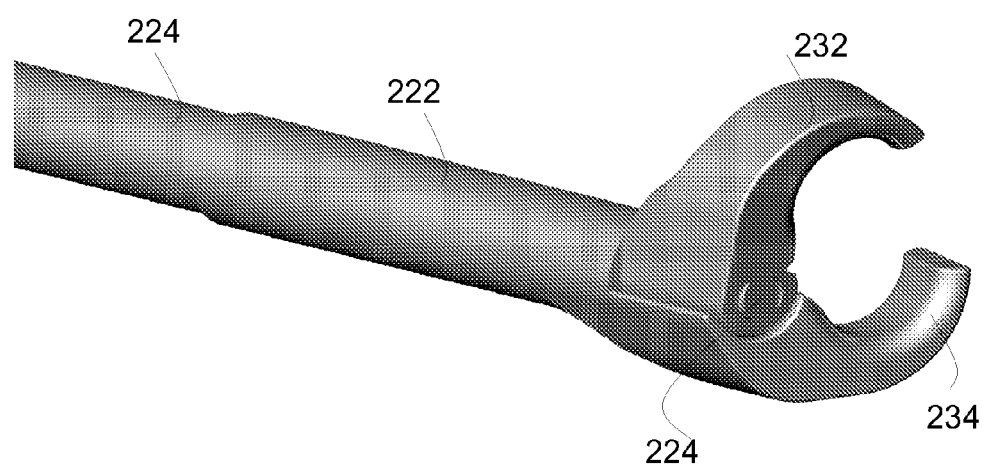
Figure 13:
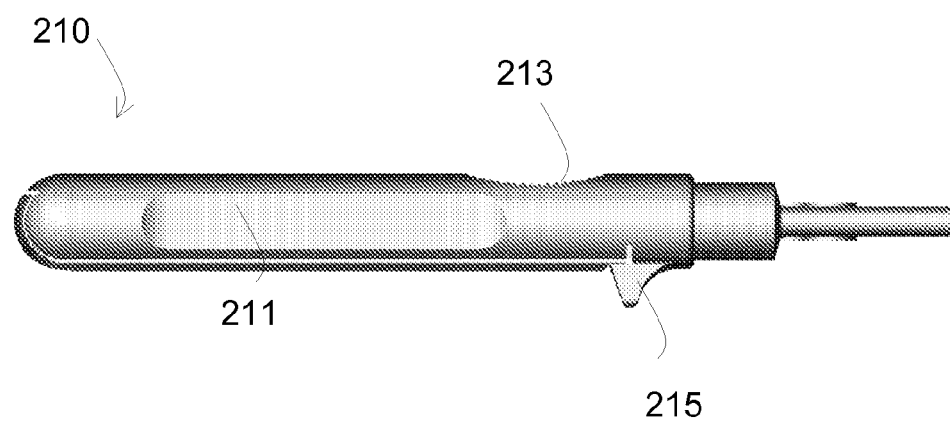
FIG. 13 is side view of the handle of the instrument of FIG. 3.
Figure 14:
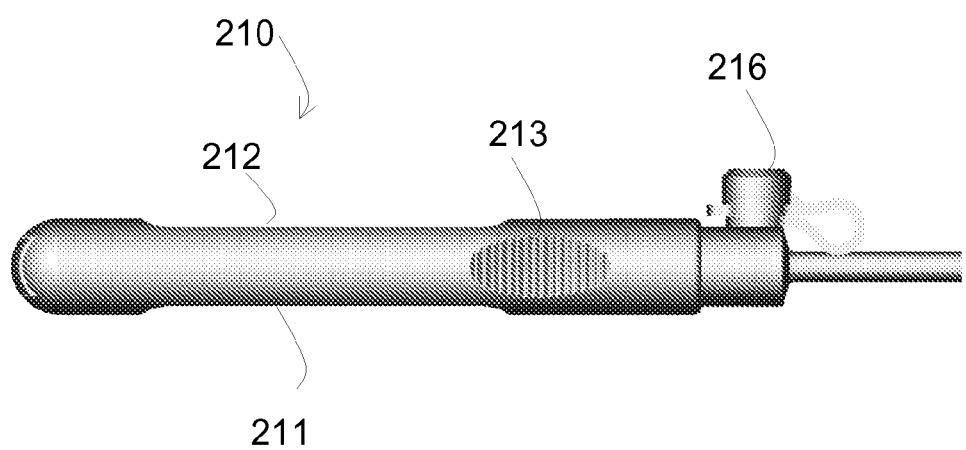
FIG. 14 is a top view of the handle of the instrument of FIG. 3.

Referring to FIG. 3, a surgical rotary capture instrument 200 includes a handle 210, an elongated shaft 220 and a distal end component 230. The handle 210 features a tactile control of the distal end component 230. Referring to FIG. 13-14 the handle 210 features a cylindrical body having a diameter of 15.9 mm and a length of 11.4 cm and it includes two side indentations 211, 212 opposite to each other and a thumb indentation 213 on the top surface. The handle 210 also features a squeeze-to-close, spring-loaded-open design. By squeezing the handle piece 215, a rack actuates a gear, developing a rotary motion that actuates a movable jaw 232 at the end component 230 through a drive shaft 224. The handle 210 also incorporates a latch 216 to keep the instrument in the closed position. The handle actuation could be any number of mechanical means that imparts the rotary motion required.

Figure 11:
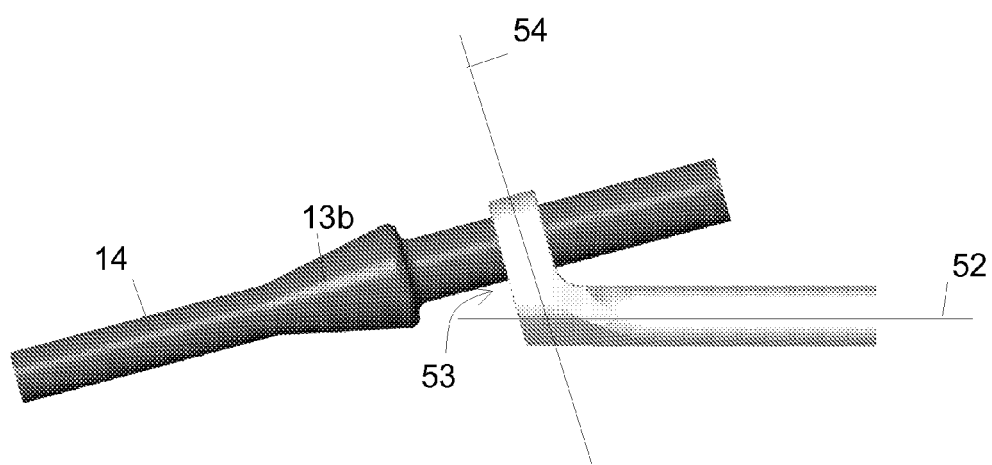
Figure 12:
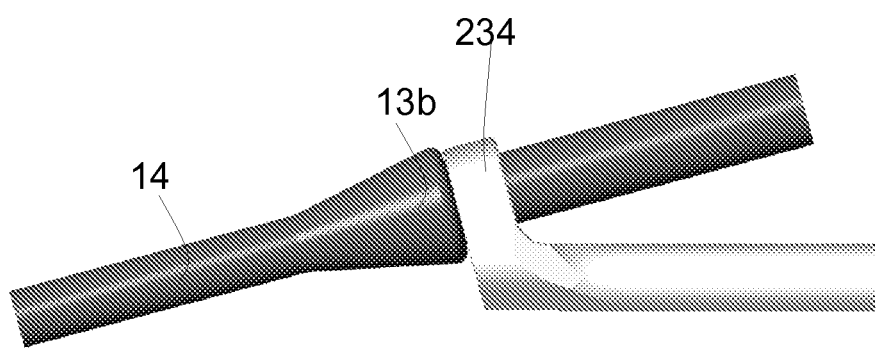
Figure 17:
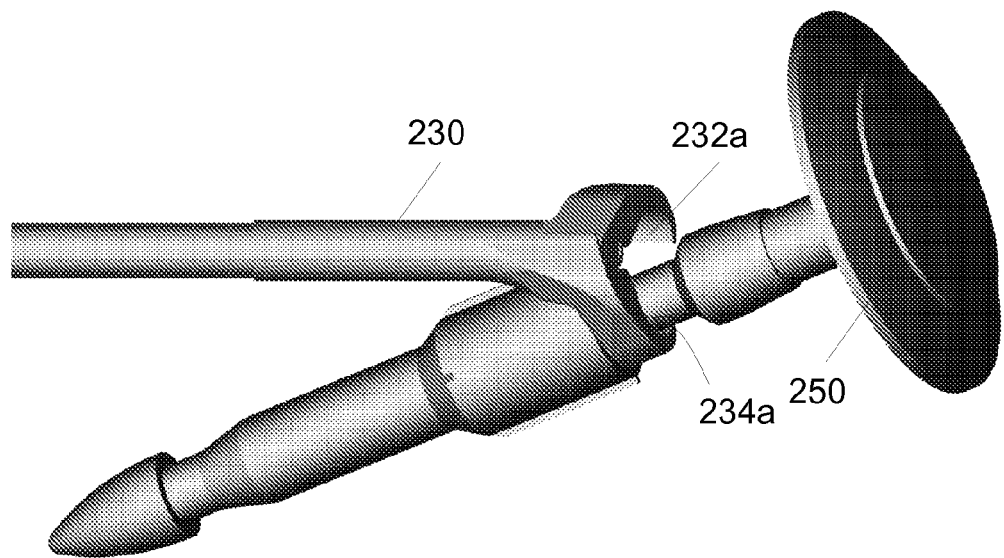
FIG. 17-FIG. 19 are perspective views of another embodiment of the rotary capture instrument of this invention.
Figure 18:
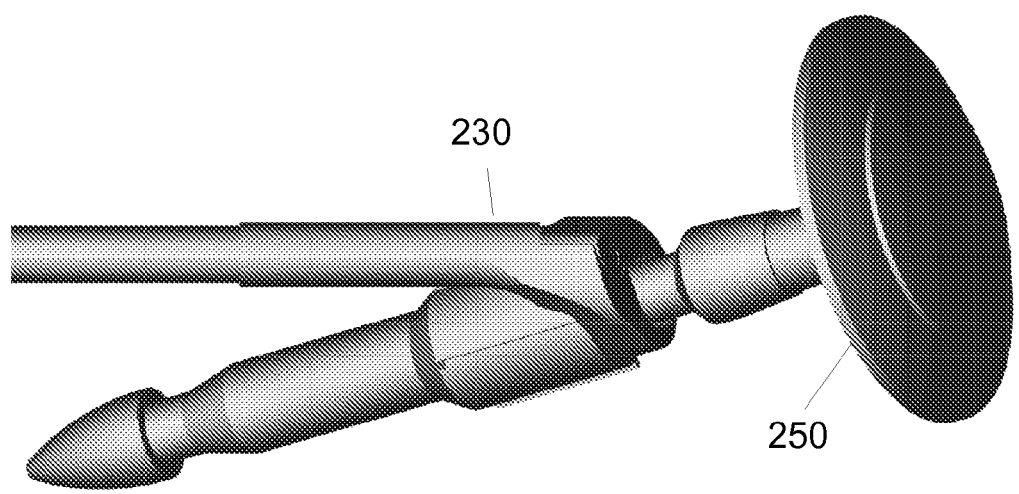
Figure 19:
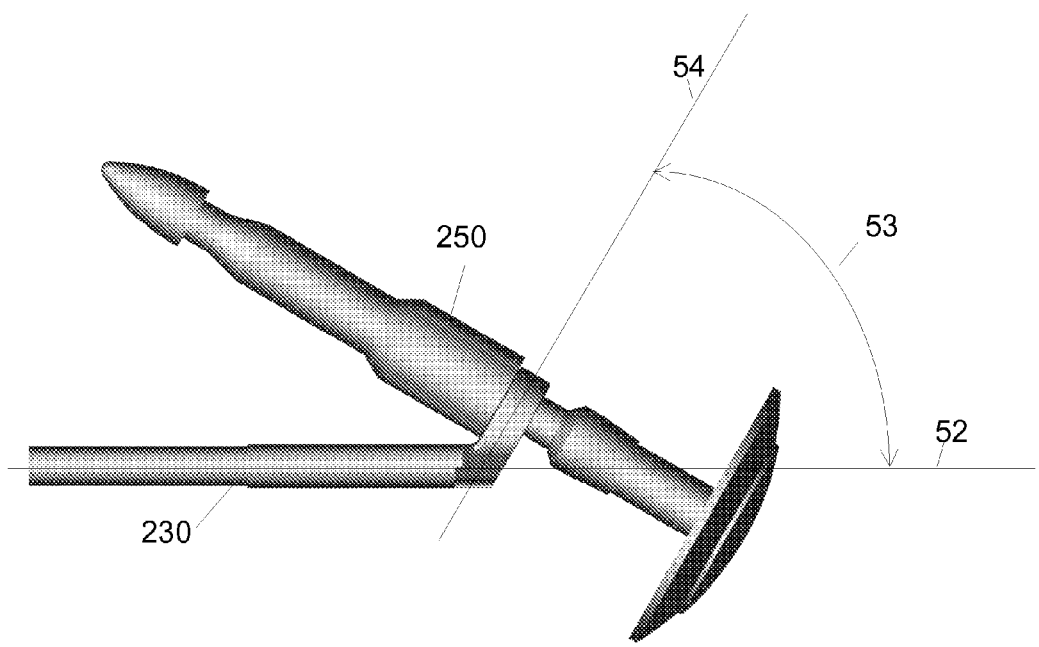

The elongated shaft 220 has a cylindrical shape and is dimensioned to fit through a laparoscopic cannula for minimally invasive surgery. In one example, the elongated shaft 220 has a length of 45 cm and a diameter of 5 mm, shown in FIG. 19. Shaft 220 includes an outer shaft 222 and an inner shaft 224. Referring to FIG. 4-12, and FIG. 17-18 the end component 230 includes a stationary jaw 234 and a movable jaw 232. The movable jaw 232 is actuated by rotary motion of the inner shaft 224. In one example, in closed position jaws 234, 232 form a circle having an inner diameter 235 of 4.8 mm and an outer diameter 236 of 7.6 mm. The front edge of opening 235 is rounded having a radius that matches the corner radius at the rear of barb 13b and the diameter of the tube 14. The rounded edge prevents the jaws from digging in and cutting into the tube 14. In the open position the maximum distance 237 between the movable jaw 232 and the stationary jaw 234 is 10.5 mm. In this embodiment, the angle 53 between the axis 52 of the elongated shaft 220 and the jaw axis 54 is 75 degrees, as shown in FIG. 11 and FIG. 17. This angle 53 may be varied depending upon the geometry of the item that needs to be grasped.

Referring to FIGS. 9-12, jaw 232 is rotated open and jaws 232, 234 are positioned around the tube 14 of the gastric band 10 adjacent to an integral conical shaped barb 13b that is intended to assist in closure. The handle 210 is then actuated causing the movable jaw 232 to rotate closed. This motion captures securely the tube 14. The diameter 240 of the barb 13b is larger than the inner diameter 235 of the closed jaws. The surgeon can then push the closed jaws 232, 234, against the integral barb 13b, thereby causing the tube 14 to move forward.

Figure 15:
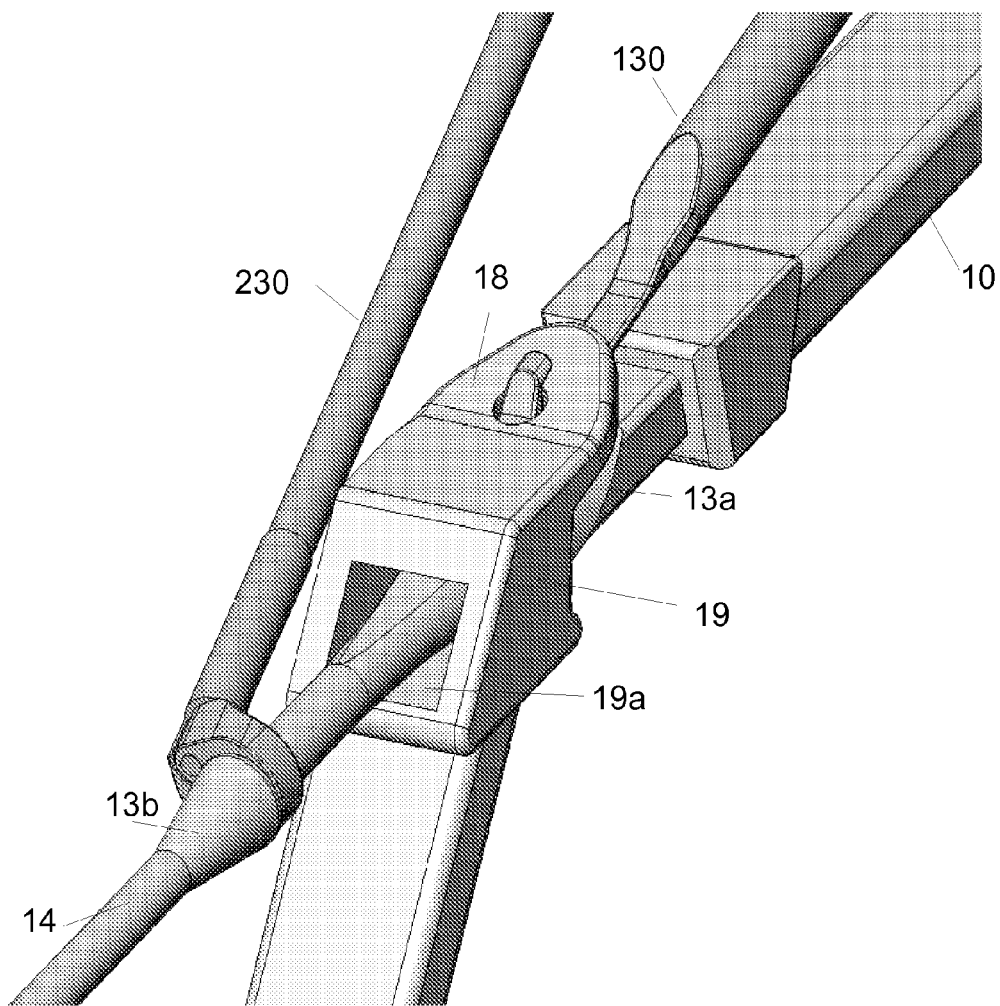
FIG. 15-FIG. 16 are perspective views of the pusher end of the instrument of FIG. 3 engaging and pushing the barb end of the gastric band of FIG. 2A through a buckle while a hook instrument is holding the buckle.
Figure 16:
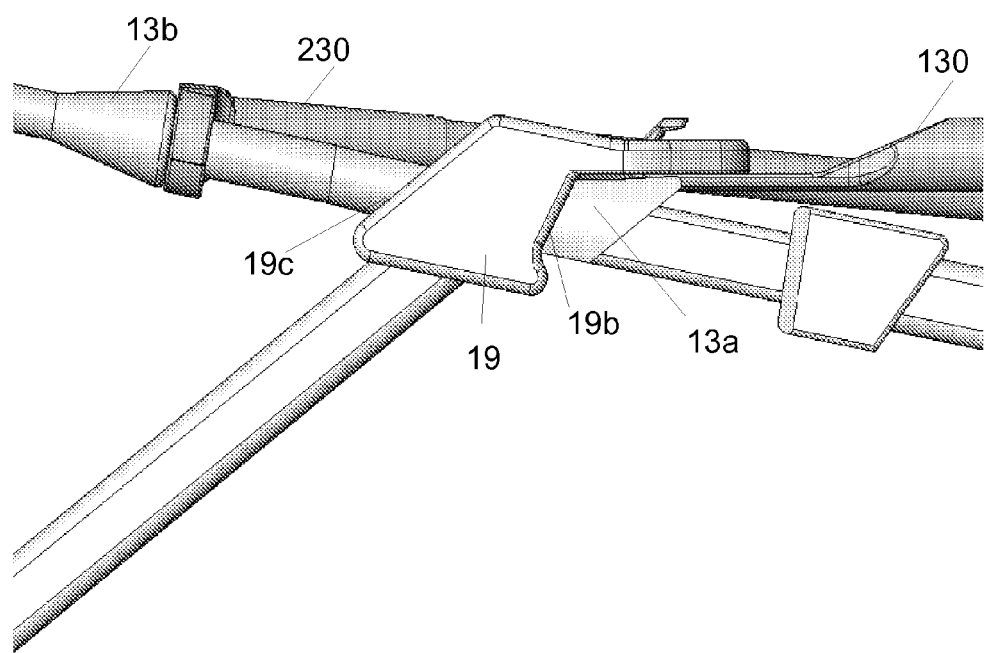

Referring to FIG. 15 and FIG. 16, the surgeon threads the tube 14 through side 19b of the buckle conduit 19a, then captures the tube 14 from the other side 19c of the buckle conduit 19a with the jaws 232, 234 and pushes the tube 14 in the direction 50 away from the buckle 19 by pushing the closed jaws 232, 234 against the barb 13b. While pushing tube 14 through the buckle conduit 19a, a hook instrument 100 is used to pull the pull tab 18 of the buckle 19. The triangular shaped member 13a of the tail portion 13 interlocks with the buckle conduit 19a and prevents the tube 14 from slipping backwards. The hook instrument 100 and the rotary capture instrument 200 apply opposing forces on the gastric band 10 in order to cinch and lock the band closed.

Figure 7:
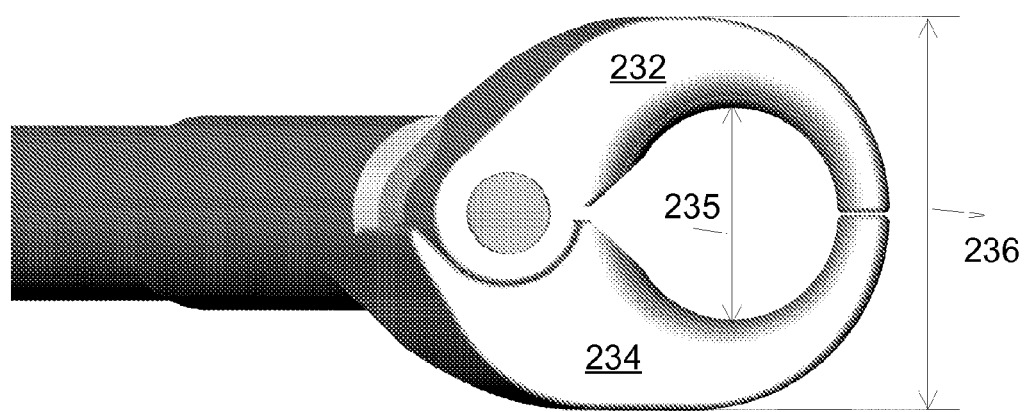
Figure 8:
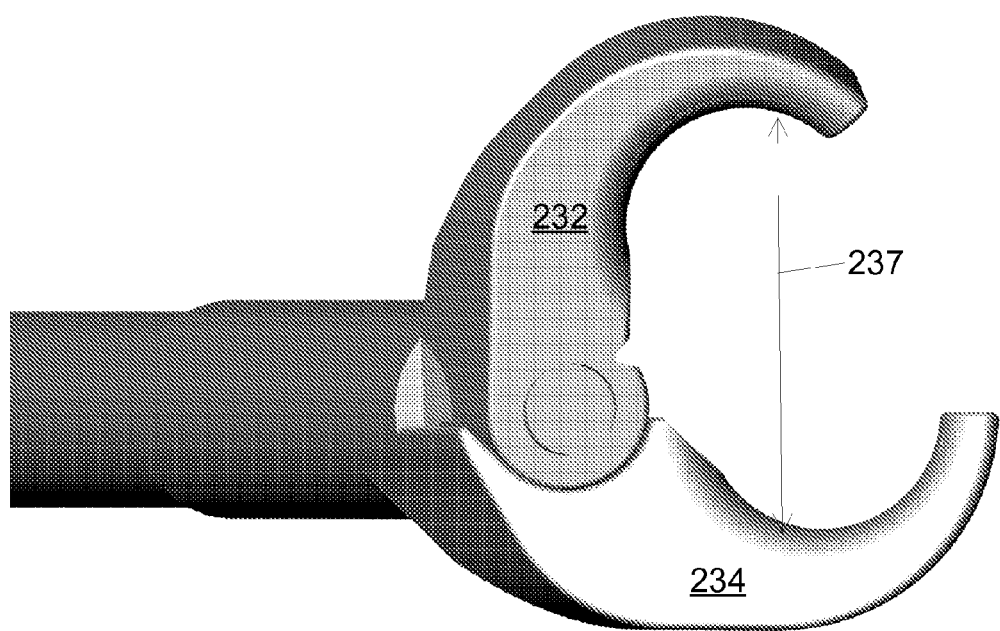
Figure 9:
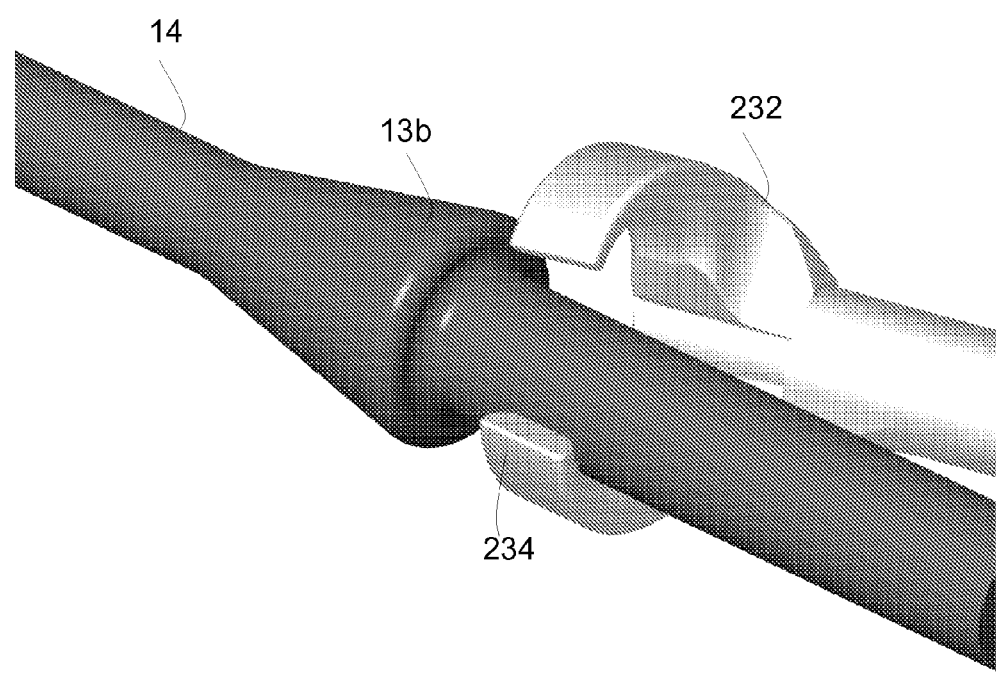
FIG. 9-FIG. 12 are perspective views of the pusher end of the instrument of FIG. 3 engaging and pushing the barb end of the gastric band of FIG. 2A.
Figure 10:
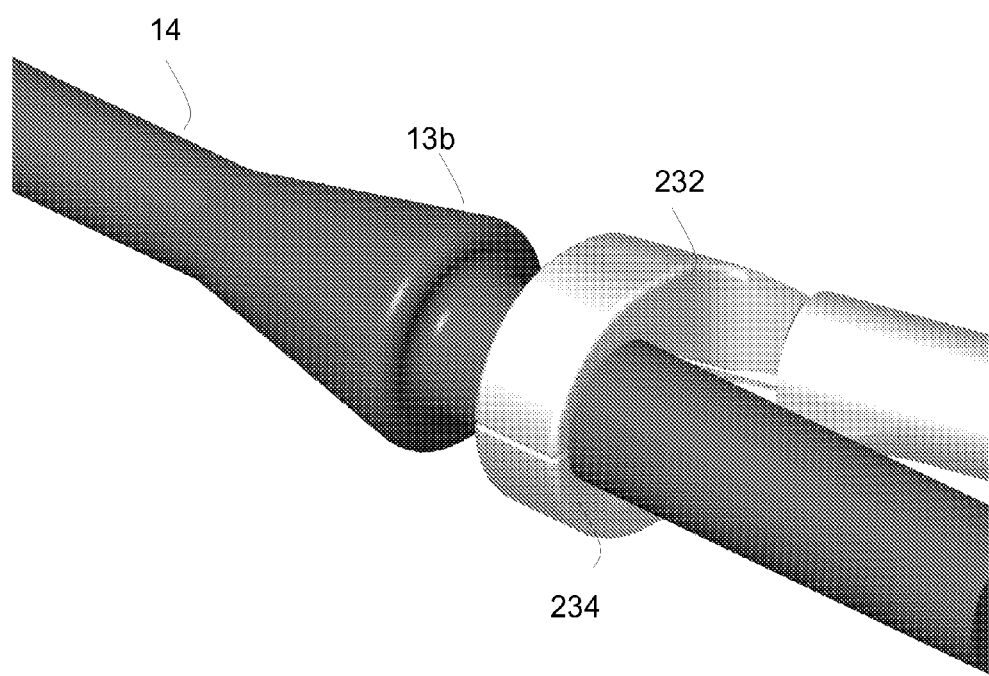

In another embodiment, the rotary capture instrument 200 of this invention is used to capture a vessel or a component, such as the anvil 250 of FIG. 17. In this case the shape of the jaws is selected so that they do not cause any damage to the component 250. This is accomplished by adjusting the angle 53 between the axis of the jaws 54 and the shaft axis 52. In one example the angle 53 is 60 degrees. The shape of the inner jaw surfaces 232a, 234a may also be varied to conform to the specific geometry of the component 250 For example, the inner surfaces 232a, 234a, may be sloped, conical, have one or more steps or have grooves that assist in grasping the component 250. The opening 235, shown in FIG. 7, is slightly larger than the diameter of the anvil stem. This allows the anvil stem to float slightly for ease of alignment with the mating stapler (not shown). Inner surfaces may also be coated with protective coatings such as Teflon.

Figure 20:
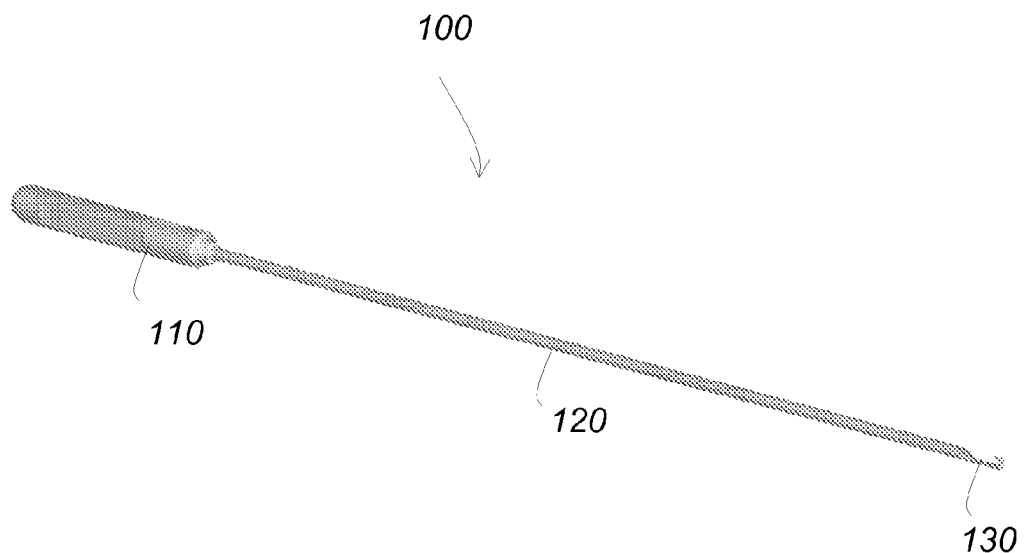
FIG. 20 is a perspective view of the endoscopic hook instrument of this invention.
Figure 21:
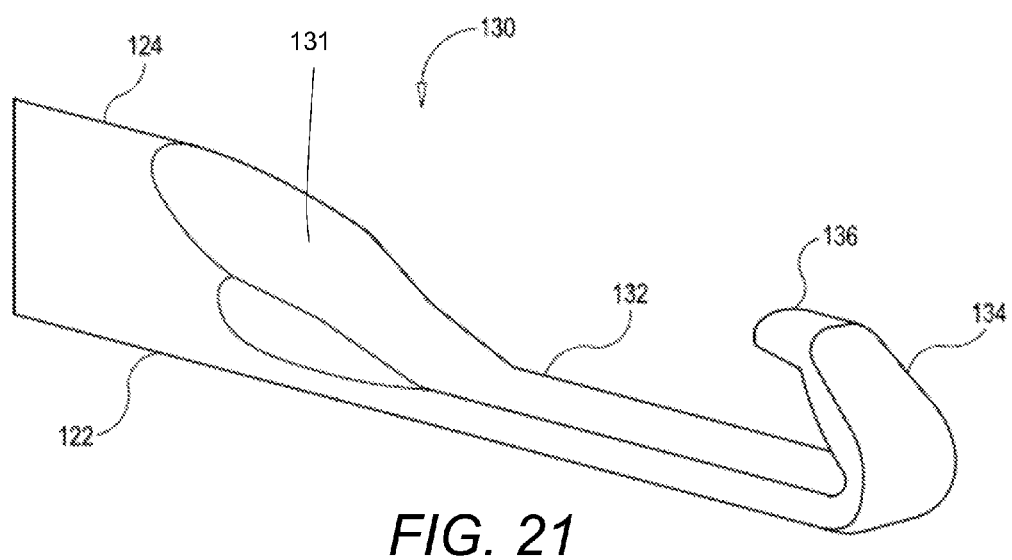
FIG. 21 is a perspective view of the hook end of the instrument of FIG. 20.
Figure 22:
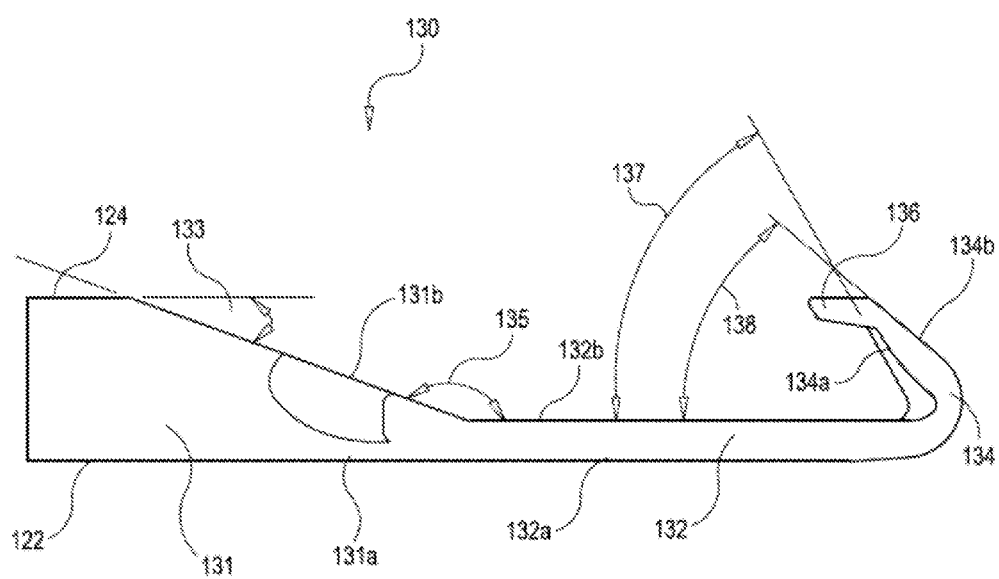
FIG. 22 is a side view of the hook of FIG. 21.
Figure 23:
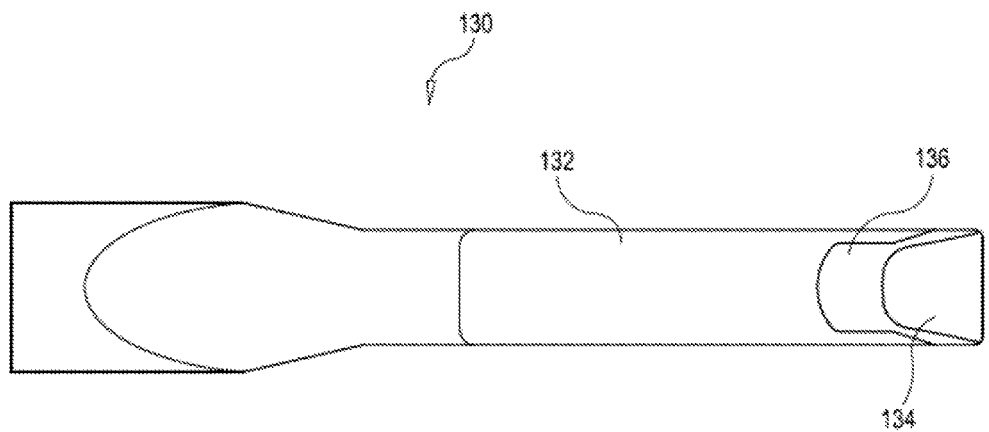
FIG. 23 is a top view of the hook of FIG. 21.
Figure 24:
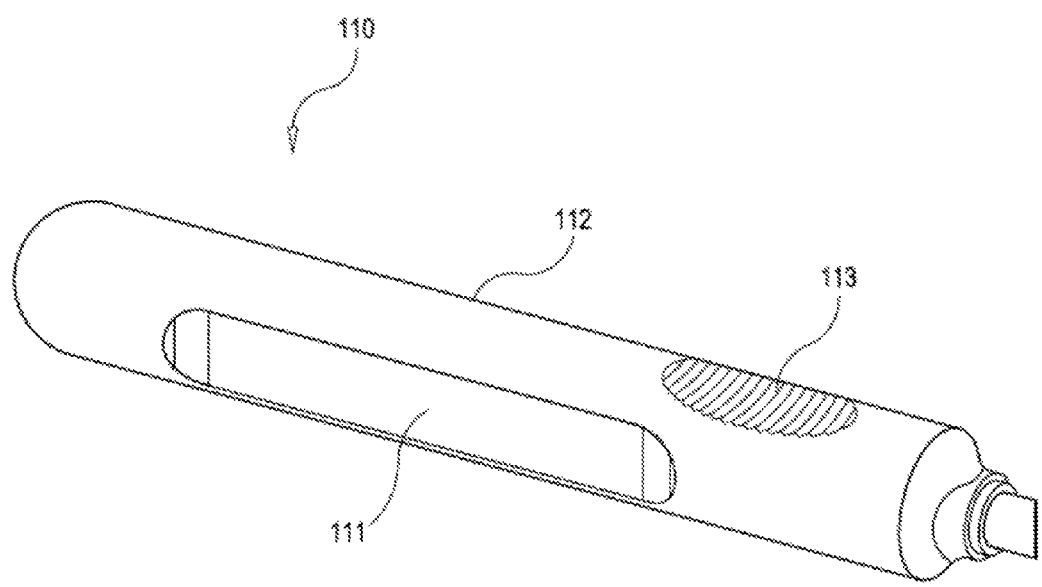
FIG. 24 is perspective view of the handle of the instrument of FIG. 20.

Referring to FIG. 20, a surgical hook instrument 100 includes a handle 110, an elongated shaft 120 and a hook end 130. The handle 110 features a tactile control of the hook end. Referring to FIG. 24 the handle 110 features a cylindrical body having a diameter of 15.9 mm and a length of 11.4 cm and it includes two side indentations 111, 112 opposite to each other and a thumb indentation 113 on the top surface. The elongated shaft 120 has a cylindrical shape and is dimensioned to fit through a laparoscopic cannula for minimally invasive surgery. In one example, the elongated shaft 120 has a length of 45 cm and a diameter of 5 mm. Referring to FIG. 21 and FIG. 22, the hook end 130 includes an angled portion, a flat portion 130 a bend portion 134 and an extension 136. The angled portion 131 has a flat bottom surface 131a and a downwards sloped top surface 131b forming an angle 133 with the top surface 124 of the elongated shaft 120. The flat portion 132 has a flat top surface 132b and a flat bottom surface 132a that extends continuously from the bottom surface 122 of the elongated shaft 120 and the bottom surface 131a of the angled portion 131. The top surface 132b of the flat portion 132 forms an angle 135 with the top surface 131b of the angled portion 131. Angles 133 and 135 are supplementary to each other, i.e., their sum is 180 degrees. In one example, angle 133 is 20 degrees and angle 135 is 160 degrees. In one example, the flat portion 132 has a thickness of 1.3 mm, a width of 3.3 mm and a length of 13.4 mm. The bend portion 134 extends from the flat portion 132 and is bend upwards and towards the handle 110. The inner surface 134a of the bend portion 134 forms an angle 137 with the top surface 132b of the flat portion 132. Inner surface 134a is formed with a radius that matches the inside of the hole 18a in the pull tab 18. This distributes the pulling force uniformly around the hole and prevents damaging of the pull tab 18 during pulling. The outer surface 134b of the bend portion 134 is curved and forms an angle 138 with the top surface 132b of the flat portion 132. In one example angles 137 and 138 are 40 and 60 degrees, respectively. Extension 136 extends from the bend portion 134, points towards the handle 110 and is parallel to the flat portion 132. In one example it has a length of 2.0 mm and a thickness of 0.8 mm. Extension 136 helps prevent slippage of the hook out of the hole 18a. The inner surface of 136 forms an angle with the inner surface 134a, which facilitates pickup of the hole 18a by the hook 130.

Figure 25:
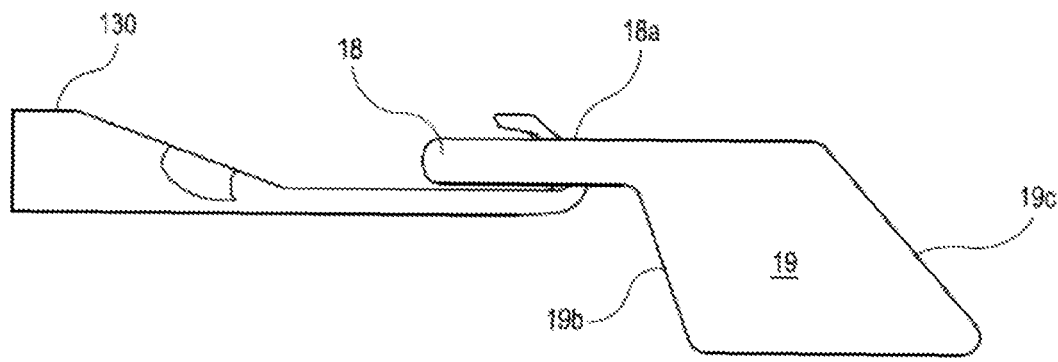
FIG. 25 is side view of the hook end of the instrument of FIG. 20 engaging the hole in the tab of the buckle of the gastric band of FIG. 2A.
Figure 26:
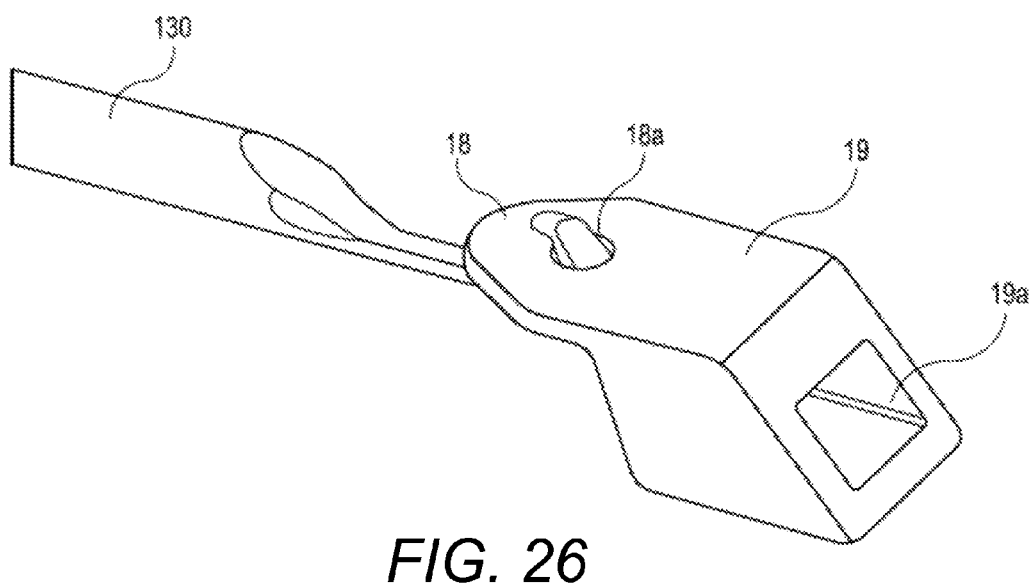
FIG. 26 is a perspective view of the hook end of the instrument of FIG. 20 engaging the hole in the tab of the buckle of the gastric band of FIG. 2A.

Referring to FIG. 25 and FIG. 26, the flat portion 132 of the hook end 130 is placed underneath the pull tab 18 of the gastric band buckle and the bend portion is inserted into the hole 18a thereby engaging the pull tab. The bend portion 134 together with the extension 136 and the flat portion 132 form a C-shaped hook that grasps securely the pull tab 18. The risk of unintentional disengagement is very low. While holding the buckle end 19 securely with the hook end 130 a rotary capture instrument 200 (shown in FIG. 15) is used to capture and push the tube 14 of the gastric band 10 through the buckle conduit 19a. The triangular shaped member 13a of the tail portion 13 interlocks with the buckle conduit 19a and prevents the tube 14 from slipping backwards. The hook instrument 100 and the rotary capture instrument 200 apply opposing forces on the gastric band 10 in order to cinch and lock the band closed.

Several embodiments of the present invention have been described. Nevertheless, it will be understood that various modifications may be made without departing from the spirit and scope of the invention. Accordingly, other embodiments are within the scope of the following claims.

What is claimed is:

1. An endoscopic surgical instrument used in minimally invasive surgery for grasping and tightening a ligature band around an internal organ, wherein said ligature band comprises an elongated strap having a buckle end and a distal end, said buckle end having an aperture and a pull tab having a hole thereon and wherein said elongated strap is configured to encircle said internal organ and said distal end is configured to pass through and lockingly engage said aperture thereby tightening said ligature band around said internal organ, the instrument comprising:
   a hook tool configured to engage said hole and pull said pull tab in a first direction while said distal end is pushed through said aperture opposite to said first direction;
   a capture tool configured to engage a protuberance of said distal end and push said distal end after it has been threaded through said aperture;
   wherein said hook tool comprises a hook having a flat portion and a bend portion extending from said flat portion and wherein said flat portion is configured to slide along a flat surface of said pull tab and said bend portion has an inner surface radius matching a radius of said hole; and
   wherein said capture tool comprises a stationary jaw and a rotationally movable jaw and wherein said rotationally movable jaw is actuated by rotational motion of an elongated shaft.

2. The endoscopic surgical instrument of claim 1 wherein said hook tool and said capture tool are configured to apply opposing forces on said ligature band for tightening said ligature band around said internal organ.

3. The endoscopic surgical capture tool of claim 1 wherein the capture tool comprises a handle; wherein said handle comprises a mechanism for actuating a rotational motion of an inner shaft, thereby actuating said rotationally movable jaw.

4. The endoscopic surgical capture tool of claim 3 wherein said mechanism comprises squeezing a handle component.

5. The endoscopic surgical capture tool of claim 3 wherein said handle comprises a cylindrical body having first and second side indentations opposite to each other and a thumb indentation on a top surface of said cylindrical body, said thumb indentation being aligned with said rotationally movable jaw.

6. The endoscopic surgical capture tool of claim 3 wherein said handle further comprises a latch for keeping said rotationally movable jaw closed.

7. The endoscopic surgical capture tool of claim 1 wherein said stationary jaw and said rotationally movable jaw comprise a material selected from a group consisting of metal, ceramic, polymer, Teflon, alloys, rubber and composites.

8. The endoscopic surgical capture tool of claim 1 wherein said stationary jaw and said rotationally movable jaw comprise inner surfaces selected from a group consisting of spherical, sloped, conical, having one or more steps and having one or more grooves.

* * * * *